US00PP29331P2

(12) United States Plant Patent
Stemkens

(10) Patent No.: US PP29,331 P2
(45) Date of Patent: May 29, 2018

(54) ***ERYSIMUM* PLANT NAMED 'ERFZ0003'**

(50) Latin Name: *Erysimum linifolium*
Varietal Denomination: ERFZ0003

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days. days.

(21) Appl. No.: 15/731,140

(22) Filed: Apr. 25, 2017

(51) Int. Cl.
*A01H 5/00* (2018.01)
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Dale Skalla

(57) ABSTRACT

A new *Erysimum* plant named 'ERFZ0003' particularly distinguished by the purple-violet flower color, dark grey green foliage color, rounded and semi-erect plant habit with good branching, and is very early to flower.

1 Drawing Sheet

Latin name of the genus and species of the plant claimed: *Erysimum linifolium.*

Varietal denomination: 'ERFZ0003'.

BACKGROUND OF THE NEW PLANT

The present invention comprises a new *Erysimum*, botanically known as *Erysimum linifolium*, and hereinafter referred to by the variety name 'ERFZ0003'.

'ERFZ0003' is a product of a planned breeding program. The new cultivar 'ERFZ0003' has purple-violet flower color, dark grey green foliage color, rounded and semi-erect plant habit with good branching, and is very early to flower.

'ERFZ0003' originates from a hybridization made in a greenhouse in April 2012 in Enkhuizen, The Netherlands. The female parent was a commercially available plant identified as 'Bowles Mauve', unpatented, with mauve flower color, fewer branches, and overall smaller size than that of 'ERFZ0003'.

The male parent of 'ERFZ0003' was an unpatented, proprietary plant identified as 'Q1108-51' with purple flower color, is earlier to flower and less vigorous than that of 'ERFZ0003'. The resultant seed was sown in September 2009 in a greenhouse in Enkhuizen, The Netherlands.

'ERFZ0003' was selected as one flowering plant within the progeny of the stated cross in March 2013 in Enkhuizen, The Netherlands.

The first act of asexual reproduction of 'ERFZ0003' was accomplished when vegetative cuttings were propagated from the initial selection in the May 2013 in a controlled environment in Enkhuizen, The Netherlands.

BRIEF SUMMARY OF INVENTION

Horticultural examination of plants grown from cuttings of the plant initiated in May 2013 in Enkhuizen, The Netherlands, and continuing thereafter, has demonstrated that the combination of characteristics as herein disclosed for 'ERFZ0003' are firmly fixed and are retained through successive generations of asexual reproduction.

'ERFZ0003' has not been observed under all possible environmental conditions. The phenotype may vary significantly with variations in environment such as temperature, light intensity, and day length.

A Plant Breeder's Right for this cultivar was applied for at the Community Plant Variety Office on Mar. 30, 2017 (2017/0909). 'ERFZ0003' has not been made publicly available more than one year prior to the filing of this application.

The following traits have been repeatedly observed and are determined to be basic characteristics of the new variety. The combination of these characteristics distinguishes this *Erysimum* as a new and distinct variety

BRIEF DESCRIPTION OF THE PHOTOGRAPHS

The accompanying photographic drawing shows typical flower and foliage characteristics of 'ERFZ0003' with colors being as true as possible with an illustration of this type.

The photographic drawing shows in

Figure 1:
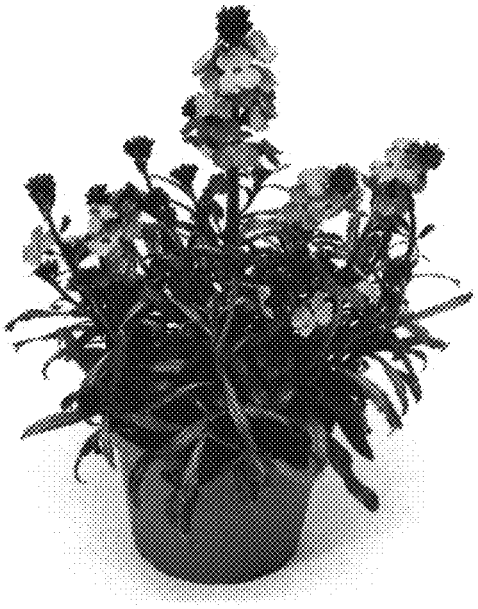

FIG. 1 a flowering plant of the new variety and in

Figure 2:
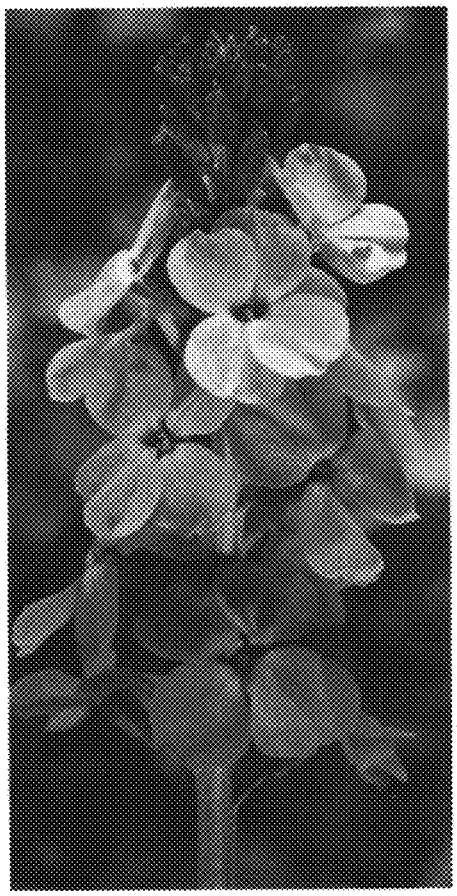

FIG. 2 a close-up of a flower and buds.

DETAILED BOTANICAL DESCRIPTION

The plant descriptions, measurements and aforementioned photographs were taken in Andijk, The Netherlands in March 2016 under natural light. These plants were growing in an indoor trial under natural light in Andijk, The Netherlands. The plants were about 22 weeks of age.

Color chart used: Royal Horticultural Society Colour Chart (R.H.S.) 2001.

TABLE 1

DIFFERENCES BETWEEN THE NEW VARIETY 'ERFZ0003' AND A SIMILAR VARIETY

| | 'ERFZ0003' | 'Bowles Mauve' (Unprotected) |
|---|---|---|
| Natural flowering response: | Much earlier | Later |
| Plant habit: | Taller when plants start to flower | Not as vigorous |
| Foliage color: | Deeper grey green | Little less green |
| Peduncle length: | Becomes longer on mature plants | Shorter |

Plant:

*Form, growth and habit*.—Compact and tightly mounded, good flowering on somewhat long peduncles at more mature stage.

*Plant height*.—32-38.0 cm.

*Plant height (inflorescence included)*.—60-65.0 cm.

*Plant width*.—About 28.0 cm.

Roots:

*Number of days to initiate roots*.—About 8 days at about 18 degrees C.

*Number of days to produce a rooted cutting*.—About 4 weeks at 18 degrees C.

*Type*.—Fine, fibrous, free branching.

*Color*.—RHS N155B.

Foliage:

*Arrangement*.—Alternate.

*Immature, leaf color, upper surface*.—Closest to RHS 147A but darker.

*Immature, leaf color, lower surface*.—Closest to RHS 137B.

*Mature, leaf color, upper surface*.—Closest to RHS 147A darker.

*Mature, leaf color, lower surface*.—Closest to RHS 137B.

*Length*.—6.9-7.5 cm.

*Width*.—0.8-1.0 cm.

*Shape*.—Narrowly oblanceolate to ensiform.

*Base shape*.—Cuneate.

*Apex shape*.—Acute to abruptly acute.

*Margin*.—Entire.

*Texture, upper surface*.—Bifid T-shaped hairs.

*Texture, lower surface*.—Bifid T-shaped hairs.

*Color of veins, upper surface*.—RHS 144C.

*Color of veins, lower surface*.—RHS 144B.

*Venation pattern*.—Pinnate.

*Petiole color*.—RHS 144C.

*Length*.—0.5-0.9 cm.

*Diameter*.—0.22 cm.

*Texture*.—Bifid T-shaped hairs.

Stem:

*Color of stem*.—RHS 144A but appears greyer due to hairs.

*Length of stem*.—17-20.0 cm.

*Diameter*.—0.42 cm.

*Length of internodes*.—1.5 cm.

*Texture*.—Bifid T-shaped hairs.

*Color of peduncle*.—RHS 144B.

*Length of peduncle*.—10.0-39.0 cm for the most mature.

*Diameter of peduncle*.—0.3-0.4 cm.

*Texture*.—Bifid T-shaped hairs.

*Color of pedicel*.—RHS 144C.

*Length of pedicel*.—0.4 cm.

*Diameter of pedicel*.—0.05 cm.

*Texture*.—Heavy covered with bifid T-shaped hairs.

Inflorescence:

*Type*.—Single, cruciform, composed of 4 petals; flowers held above the plant, relatively long peduncles on more mature plants.

*Natural flowering season*.—March to October in The Netherlands.

*Quantity of inflorescences per plant*.—23-25 with open flowers and 24-29 immature ones.

*Lastingness of individual blooms on the plant*.—About 4 days.

*Fragrance*.—None.

Bud (just before opening/showing color):

*Color*.—Some RHS 155B and some closer to RHS 84C.

*Length*.—1.1 cm.

*Width*.—0.4-0.5 cm.

*Shape*.—Oblong.

Corolla:

Immature inflorescence:

*Diameter*.—1.2-1.4 cm.

*Color of petals, upper surface*.—RHS N81A.

*Color of petals, lower surface*.—RHS N81B.

Mature inflorescence:

*Flower diameter*.—1.5-1.7 cm.

*Depth*.—1.3-1.4 cm.

*Petal color, upper surface*.—RHS N81C.

*Petal color, lower surface*.—RHS N81C.

*Length of petal*.—0.8-0.9 cm.

*Width of petal*.—0.7-0.8 cm.

*Shape*.—Spathulate.

*Apex shape*.—Slightly retuse.

*Petal base*.—Acuminate.

*Margin*.—Entire.

*Petal texture, upper surface*.—Papillose.

*Petal texture, lower surface*.—Papillose.

Calyx:

*Quantity*.—4 sepals.

*Color, upper surface*.—RHS 137B.

*Color, lower surface*.—RHS 137B.

*Sepals*.—

*Length*.—0.6 cm.

*Width*.—0.3 cm.

*Shape*.—Broadly oblong.

*Apex shape*.—Obtuse.

*Base*.—Cuneate.

*Margins*.—Entire.

*Texture, upper/inner surface*.—Glabrous.

*Texture, lower/outer surface*.—Bifid T-shaped hairs.

Reproductive organs:

*Gynoecium*.—

*Pistil quantity*.—1.

*Length*.—0.6 cm.

*Style color*.—RHS 145C.

*Style length*.—0.45-0.5 cm.

*Style texture*.—Heavily covered with bifid hairs as to appear much lighter in color.

*Stigma color*.—RHS 145B.

*Stigma shape*.—Oval to disc-shaped and a cleft down the center.

*Stigma texture*.—Very grainy looking.

*Ovary color*.—Not developed enough at this time to observe.

*Androecium.*—

*Stamens, quantity.*—6.

*Color of filaments.*—Closest to RHS 160D and somewhat translucent.

*Length filaments.*—0.6 cm.

*Anther color.*—RHS 18B.

*Anther length.*—0.3 cm.

*Anther shape.*—Oblong.

*Color of pollen.*—RHS 18B.

*Pollen amount.*—Normal.

*Fertility/seed set.*—Has not been determined to date.

*Disease/pest resistance.*—Has not been determined to date.

What is claimed is:

1. A new and distinct variety of *Erysimum* plant named 'ERFZ0003' substantially as illustrated and described herein.

* * * * *